United States Patent
Koller

(10) Patent No.: US 10,329,731 B2
(45) Date of Patent: Jun. 25, 2019

(54) METHOD OF OPERATING A MOBILE WORK MACHINE WITH A GROUND PRESSURE LIMITATION

(71) Applicant: Liebherr-Werk Nenzing GmbH, Nenzing (AT)

(72) Inventor: Alfred Koller, Altach (AT)

(73) Assignee: Liebherr-Werk Nenzing GmbH, Nenzing (AT)

( * ) Notice: Subject to any disclaimer, the term of this patent is extended or adjusted under 35 U.S.C. 154(b) by 0 days.

(21) Appl. No.: 15/557,386

(22) PCT Filed: Feb. 26, 2016

(86) PCT No.: PCT/EP2016/000334
§ 371 (c)(1),
(2) Date: Sep. 11, 2017

(87) PCT Pub. No.: WO2016/142038
PCT Pub. Date: Sep. 15, 2016

(65) Prior Publication Data
US 2018/0245304 A1    Aug. 30, 2018

(30) Foreign Application Priority Data
Mar. 12, 2015 (DE) .................. 10 2015 003 177

(51) Int. Cl.
*B66C 13/46* (2006.01)
*B66C 23/90* (2006.01)
(Continued)

(52) U.S. Cl.
CPC .............. *E02D 11/00* (2013.01); *B66C 13/46* (2013.01); *B66C 23/36* (2013.01); *B66C 23/90* (2013.01);
(Continued)

(58) Field of Classification Search
CPC ......... E02D 11/00; E02D 1/022; B66C 13/46; B66C 23/36; B66C 23/90; B66C 23/905; G01M 5/00; G01N 3/08
See application file for complete search history.

(56) References Cited

U.S. PATENT DOCUMENTS 3,713,129 A * 1/1973 Buchholz .............. B66C 23/905
                                                       212/277
4,216,868 A * 8/1980 Geppert ................ B66C 23/905
                                                       212/278
(Continued)

FOREIGN PATENT DOCUMENTS

DE    19612423 A1    10/1997
DE    20100489 U1     5/2002
(Continued)

OTHER PUBLICATIONS

WSH Council; Creating Lifiting Plan Guidelines—WG Draft for Industry and POublic Comment; Guidelines for Creating Lifting Plan for Lifting Operations in Workplaces; Aug. 31, 2014 (Year: 2014).*

(Continued)

*Primary Examiner* — Benjamin F Fiorello
(74) *Attorney, Agent, or Firm* — McCoy Russell LLP

(57) ABSTRACT

The invention relates to a method of operating a mobile work machine with a ground pressure limitation and to a corresponding work machine. A maximum permitted ground pressure is compared with an actually present ground pressure.

15 Claims, 3 Drawing Sheets

(51) Int. Cl.
*E02D 11/00* (2006.01)
*E02D 1/02* (2006.01)
*G01N 3/08* (2006.01)
*B66C 23/36* (2006.01)
*G01M 5/00* (2006.01)

(52) U.S. Cl.
CPC ............ *B66C 23/905* (2013.01); *E02D 1/022* (2013.01); *G01M 5/00* (2013.01); *G01N 3/08* (2013.01)

(56) References Cited

U.S. PATENT DOCUMENTS

| | | | | |
|---|---|---|---|---|
| 4,516,116 | A | * | 5/1985 | White ................... B66C 23/905 340/665 |
| 5,393,172 | A | * | 2/1995 | Akesaka ................ E21B 7/208 299/56 |
| 6,587,795 | B2 | * | 7/2003 | Schmid ................ B66C 23/905 212/278 |
| 7,012,540 | B2 | * | 3/2006 | Petzold ................... B66C 23/78 340/440 |
| 7,378,950 | B2 | * | 5/2008 | Lehnen ..................... B66C 3/04 212/277 |
| 9,365,398 | B2 | * | 6/2016 | Benton ................... B66C 23/88 |
| 2008/0210505 | A1 | * | 9/2008 | Vigholm ............... E02F 9/2207 188/266.2 |

FOREIGN PATENT DOCUMENTS

| | | |
|---|---|---|
| DE | 10110176 A1 | 9/2002 |
| DE | 10320382 A1 | 12/2004 |
| DE | 102012019850 A1 | 4/2014 |
| JP | H03115090 A | 5/1991 |

OTHER PUBLICATIONS

ISA European Patent Office, International Search Report Issued in Application No. PCT/EP2016/000334, dated Jun. 7, 2016, WIPO, 4 pages.

* cited by examiner

METHOD OF OPERATING A MOBILE WORK MACHINE WITH A GROUND PRESSURE LIMITATION

CROSS-REFERENCE TO RELATED APPLICATION

The present application is a U.S. National Phase of International Patent Application Serial No. PCT/EP2016/000334, entitled "MACHINE," filed on Feb. 26, 2016. International Patent Application Serial No. PCT/EP2016/000334 claims priority to German Patent Application No. 10 2015 003 177.5, filed on Mar. 12, 2015. The entire contents of each of the above-mentioned applications are hereby incorporated by reference in their entirety for all purposes.

TECHNICAL FIELD

The present invention relates to a method of operating a mobile work machine with a ground pressure limitation and to a corresponding work machine.

BACKGROUND AND SUMMARY

Mobile work machines are known from the prior art and serve, for example, to move loads or to perform mechanical work. It may be necessary in this respect to support the respective work machine for carrying out the work correspondingly on the ground. If this is done incorrectly, it can occur that the work machine topples over. In particular pole machines and cranes having long booms are particularly at risk in this respect. The error cause is in this respect often not only an exceeding of the permitted payload of the work machine, but rather a yielding of the subsurface long before the reaching of the maximum permitted payload of the work machine. There are currently no means of comparing the then current load carrying capacity of the ground with the ground pressure generated in the then current load state and thus of avoiding a yielding of the subsurface.

The estimation of the subsurface is difficult for the unit operator. The subsurface is typically determined beforehand by a geologist or by another expert, frequently while using various measurement devices.

It is therefore the object of the present invention to provide a work machine or a method in which the toppling over of the work machine is prevented due to a yielding subsurface.

This object is achieved by a method of operating a mobile work machine with a ground pressure limitation, comprising the steps: determining a maximum permitted ground pressure; calculating the actual ground pressure; comparing the calculated actual ground pressure with the maximum permitted ground pressure; and reporting the comparison result to the operator of the work machine and/or stopping a movement of the work machine that increases the ground pressure on an exceeding of a limit value of the actual ground pressure.

A ratio between the maximum tolerable ground pressure and the actually generated ground pressure can in this respect advantageously be made known to the operator at the then current unit position or work machine position. Not only a ground pressure can in this respect be delivered as operator information in the form of a number, but also or alternatively a color display having the colors green/yellow/red, with green indicating a permitted load, red indicating a non-permitted load, and yellow indicating a border load between a permitted load and a non-permitted load. A percentage-wise feedback is also conceivable in which the percentage of the maximum permitted ground pressure being reached is indicated.

In a further preferred embodiment, it is conceivable that a manual input is carried out by the operator and/or an automatic measurement of the maximum permitted ground pressure is carried out in the method of determining the maximum permitted ground pressure.

It is conceivable in a further preferred embodiment that a setting of the unit configuration of the work machine is carried out, in particular by the operator. The method in accordance with the invention can hereby advantageously be correspondingly adapted to a converted or modified work machine. A setting of the unit configuration can also take place automatically via corresponding sensors.

It is conceivable in a further preferred embodiment that a detection of the then current geometry of the work machine is carried out. The then current geometry can in this respect vary, for example, in that booms are extended or retracted or that supports are repositioned. If the geometry of the work machine varies during a work procedure in this respect, it is advantageously possible to react thereto in real time and to adapt the method correspondingly dynamically. The detection of the then current geometry of the work machine can in this respect also take place automatically, for example via corresponding sensors.

It is conceivable in a further preferred embodiment that a detection of the then current load of the work machine is carried out and/or that a calculation of the load of the work machine is carried out. A dynamic adaptation of the corresponding parameters within the method procedure can advantageously thus be carried out. If the load of the work machine or its strain changes, for example due to work movements of the work machine or changed wind conditions or similar factors, it is thus possible in accordance with the method to take this into account in the ground pressure limitation.

It is conceivable in a further preferred embodiment that the setting of the unit configuration of the work machine comprises the setting of a ballast and/or of a pole length and/or the setting of further components of the work machine.

The present invention also relates to a work machine, in particular to a pile driver and/or to a drill, having an apparatus for carrying out a method, comprising the steps: determining a maximum permitted ground pressure; calculating an actual ground pressure; comparing the calculated actual ground pressure with the maximum permitted ground pressure; and reporting the comparison result to an operator of the work machine and/or stopping a movement of the work machine that increases the ground pressure on an exceeding a limit value of the actual ground pressure.

It is conceivable in this respect in a particularly preferred embodiment that a sensor apparatus known, for example, from the prior art such as from DE 20 100 489 U1 is provided for an automatic measurement of the maximum permitted ground pressure.

Further details and advantages of the invention will be shown with reference to the Figures.

DETAILED DESCRIPTION

In accordance with the method, the current unit configuration (pole length, ballast, etc.) is set by the driver or the operator of the work machine in a step analog to the load torque limitation of crawler cranes and the then current unit load is determined and the ground pressure calculated by a calculation model and corresponding sensors. Corresponding load torque limiters taking account of the ground pressure of the machine are known from the prior art.

What is important is that, in addition to the detection and limitation of the load torque, the ground pressure calculated therefrom is compared with a limit value.

The limit value can either be a limit value that corresponds to the respective construction site conditions and that is to be input manually (e.g. determined by an expert), or it is conceivable in a further consequence to determine the maximum permitted ground pressure continuously by the unit. Corresponding sensor systems have to be provided accordingly.

The comparison of the ground pressure currently produced by the unit with the limit value should be displayed to the operator (green/yellow/red, percentage or the like).

An exceeding of the limit value can likewise be prevented by the load torque limitation (→additional switch-off criterion).

The major innovations are therefore the comparison of the ground pressure with a limit value and the taking into account of the tolerable ground pressure as a new switch-off criterion.

It is thereby possible to determine the maximum exploitation of the unit on a subsurface capable of providing support and to accordingly visualize it to the operator, on the one hand; on the other hand, an impending failure of the subsurface can be recognized at an early point in time and a toppling over of the unit can thus be avoided in many cases.

Figure 1:
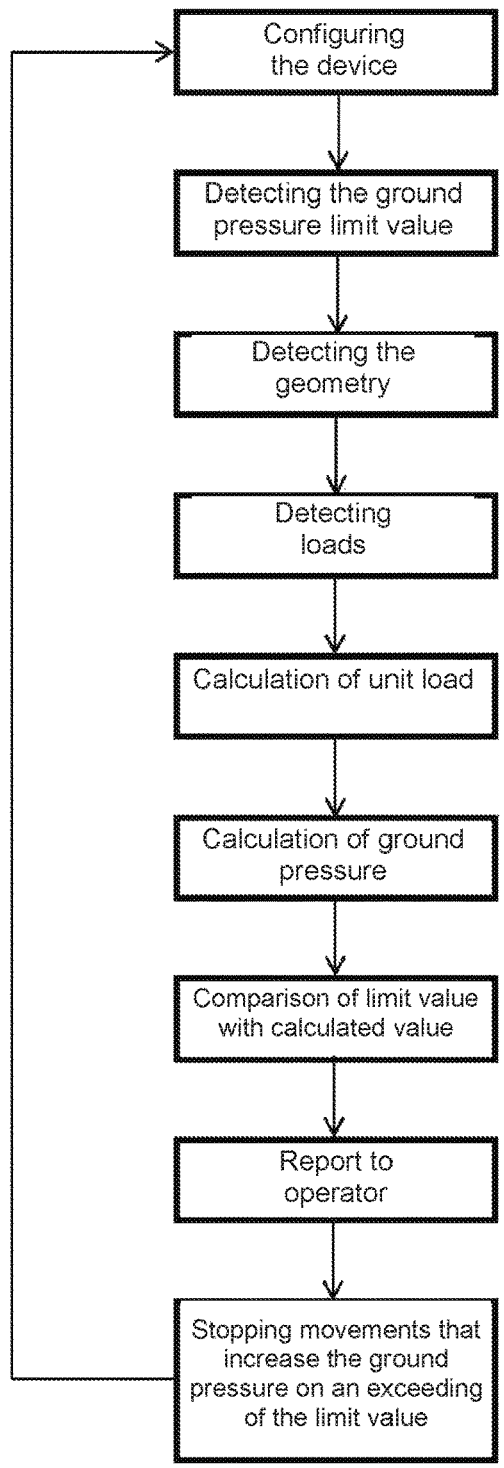
FIG. 1 shows a schematic workflow of a method in accordance with the invention.

The present invention will now be described in more detail while referring to the embodiment shown in FIG. 1. The method procedure in accordance with FIG. 1 is in this respect not to be understood as compulsory. Where this does not contradict the basic idea of the invention, the individual steps can also run in a different order or can be completely dispensed with. In accordance with the flowchart of FIG. 1, the unit or the work machine is first configured in accordance with the method in an embodiment of the invention. In particular in accordance with the method in this respect, the ballast, the pole length in the case of a pile driver, the mode of operation of the work unit or of the work machine or other parameters can be configured. It is conceivable that the configuration is carried out manually by the operator or that special sensors are provided for the configuration that automatically detect the then current configuration of the work machine. The configuration can also be carried out in part via sensors and in part manually by the operator.

In a further step, a limit value of the permitted ground pressure can then be detected. A manual input by the driver or by the operator of the work unit can take place for this purpose. It is equally alternatively or additionally conceivable that measurements by the work unit or by auxiliary units are carried out by means of a suitable sensor system for detecting the limit value of the permitted ground pressure. It is furthermore conceivable to transmit the permitted limit value from the construction site manager by means of a common data transmission device from an external data processing machine to the machine control and to display it to the operator. Mobile construction machines are frequently equipped with apparatus for position determination (e.g. GPS, DGPS). It can thereby be recognized when such a machine drives into a region on the construction site in which due to geological or construction circumstances (cavities, sewers, etc. in the subsurface) a different limit value is permitted for the ground pressure. The then currently permitted limit value can then advantageously automatically be transmitted to the machine and shown on the display.

In a further step, the geometry of the work unit can be detected, with the outreach and the tilt of the work unit in particular being able to be taken into consideration. The geometry of the work unit can in this respect also mean the design or the arrangement of the individual components of the unit. Supports that may be present to support the unit and the outreach of the supports are equally covered in this respect as are the boom or ballast weights.

Provision can be made in a further step that loads on the work machine are detected, with the measurement being able to take place, for example, via various control cables and/or cylinder pressures. Loads can in this respect mean a weight that is moved by the work machine during its usual work activity. In this respect, it can be the weight of parts of the machine itself and/or the weight of moving conveyed products.

Provision can be made in a further step that a calculation of the unit load takes place, with algorithms known per se being able to be used. In this respect, that load is especially relevant that is introduced into the parts of the machine that serve the support of the machine. It can in this respect be supports and/or parts of the chassis, for example.

The calculation of the ground pressure can take place in a further step by using further algorithms known per se. If the load of the unit has been determined in the previous step, the actual ground pressure can be calculated while taking account of the bearing area of the machine.

The previously detected limit value can furthermore be compared with the calculated value of the ground load in a further step for the carrying out of the ground pressure limitation in accordance with the method. A corresponding report to the operator can take place from this comparison in a further step. A procedure naturally has to be followed in this respect such that the operator is correspondingly warned or informed in good time before a reaching of critical situations in which the actually applied ground pressure comes close to the maximum permitted ground pressure.

It is furthermore optionally possible in accordance with the method to instigate a stopping of the movement that increases the ground pressure on an exceeding of the permitted limit value. It is conceivable for this purpose that movements carried out by the work machine are detected in accordance with the method. If it is then found that a permitted limit value has been exceeded, the last movement carried out by the work machine can, for example, be stopped in accordance with the method. Further movements or movements different than the last carried out movement can naturally also stopped.

Figure 2:
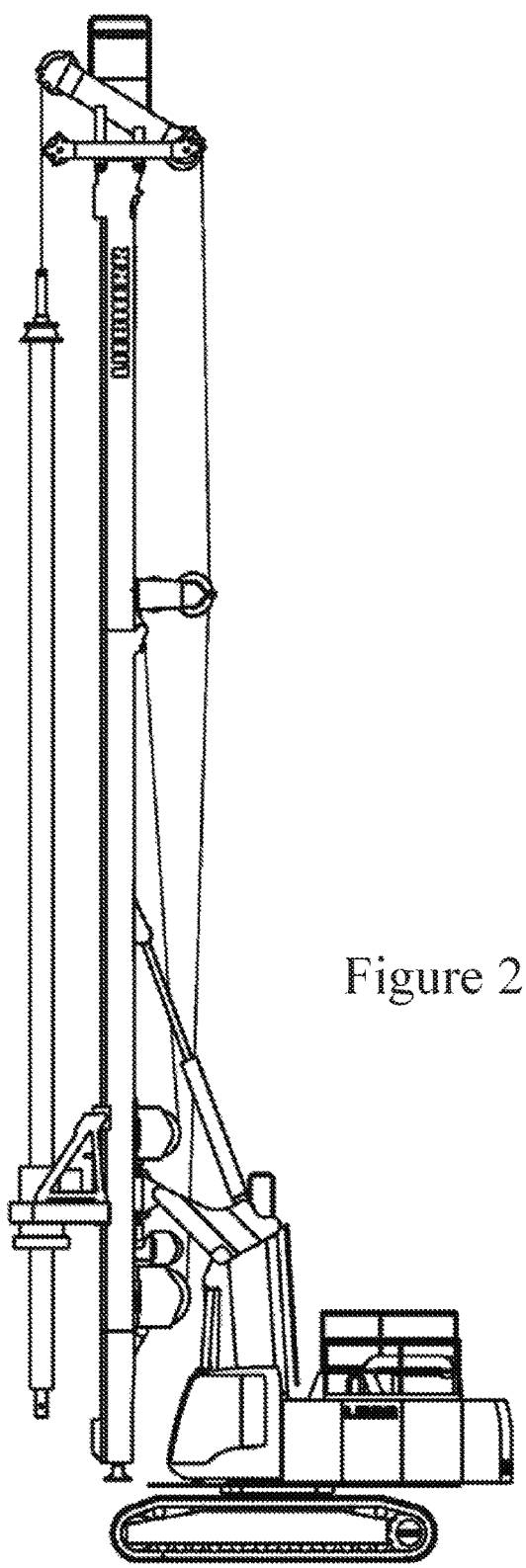
FIG. 2 shows a work machine.

FIG. 2 shows an exemplary work machine, with a pile driver and/or a drill being shown in the present case.

Figure 3:
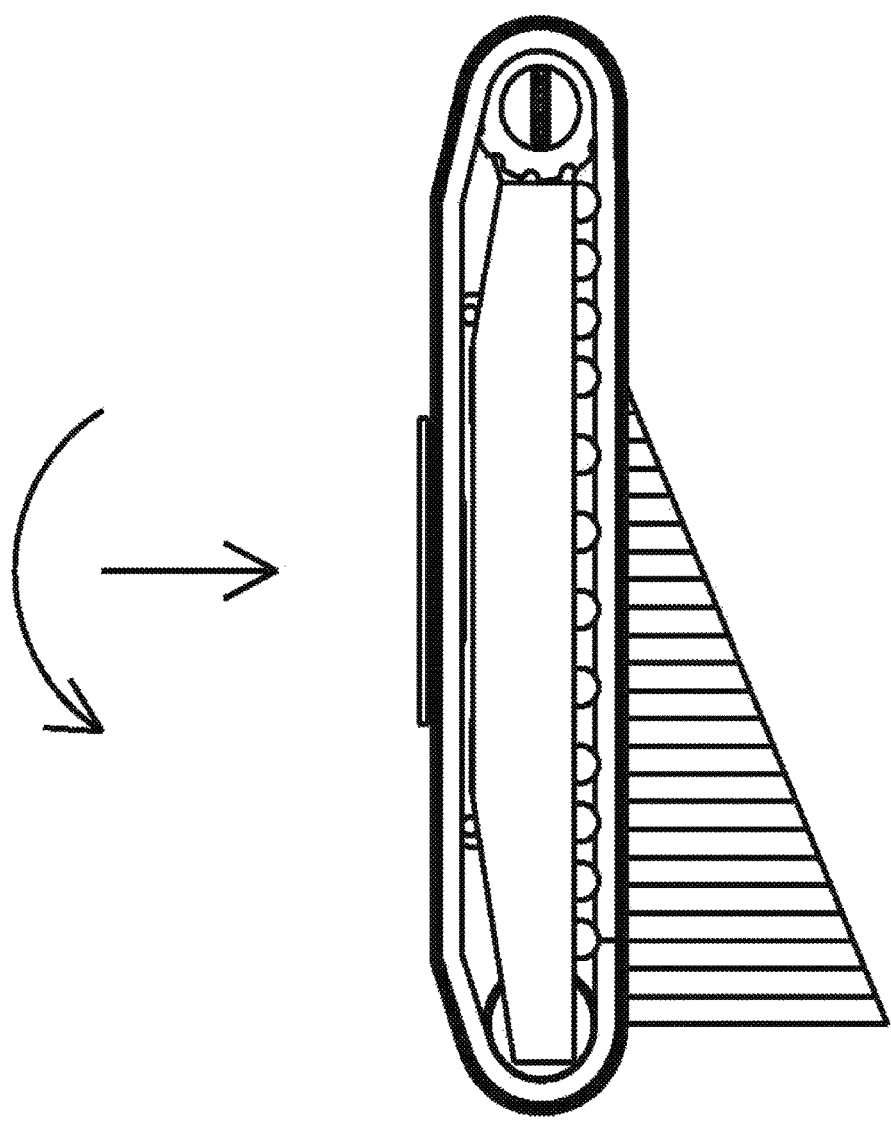
FIG. 3 shows a schematic representation of the ground pressure with a work machine.

In accordance with FIG. 3 in this respect a possible ground pressure distribution beneath the work unit is shown schematically. It is indicated by the arrows of FIG. 3 that both a weight load and a torque caused by the weight and the mode of operation of the work unit act on the ground through the work unit. In accordance with the method, this ground pressure can be limited.

The invention claimed is:

1. A method of operating a mobile work machine with a ground pressure limitation, comprising the steps:
   detecting a current unit load of the mobile work machine via sensors;
   determining a maximum permitted ground pressure;
   calculating an actual ground pressure based on the current unit load;
   comparing the calculated actual ground pressure with the maximum permitted ground pressure; and
   reporting the comparison result to an operator of the mobile work machine via a visualization and/or stopping a movement of the mobile work machine that increases the ground pressure on an exceeding a limit value of the actual ground pressure.

2. The method in accordance with claim 1, wherein a manual input by the operator and/or an automatic measurement of the maximum permitted ground pressure is carried out to determine the maximum permitted ground pressure.

3. The method in accordance with claim 2, wherein a setting of a unit configuration of the mobile work machine is carried out by the operator.

4. The method in accordance with claim 1, wherein a setting of a unit configuration of the mobile work machine is carried out by the operator, the setting of the unit configuration of the mobile work machine comprises a setting of a ballast and/or of a pole length.

5. The method in accordance with claim 4, wherein a detection of a geometry of the mobile work machine is carried out, the geometry of the mobile work machine including one or more of outreach and tilt of the mobile work machine.

6. The method in accordance with claim 4, wherein a calculation of a load of the mobile work machine is carried out.

7. The method in accordance with claim 1, wherein a detection of a geometry of the mobile work machine is carried out, the geometry of the mobile work machine including one or more of outreach and tilt of the mobile work machine.

8. The method in accordance with claim 7, wherein a setting of a unit configuration of the mobile work machine comprises a setting of a ballast and/or of a pole length of the mobile work machine.

9. The method in accordance with claim 1, wherein a detection of a load of the mobile work machine is carried out.

10. The method in accordance with claim 9, wherein a setting of a unit configuration of the mobile work machine comprises a setting of a ballast and/or of a pole length of the mobile work machine.

11. The method in accordance with claim 1, wherein a calculation of a load of the mobile work machine is carried out.

12. The method in accordance with claim 11, wherein a setting of a unit configuration of the mobile work machine comprises a setting of a ballast and/or of a pole length of the mobile work machine.

13. A work machine having an apparatus for carrying out a method, comprising the steps:
   detecting a current unit load of the work machine via sensors;
   determining a maximum permitted ground pressure;
   calculating an actual ground pressure based on the current unit load;
   comparing the calculated actual ground pressure with the maximum permitted ground pressure; and
   reporting the comparison result to an operator of the work machine and/or stopping a movement of the work machine that increases the ground pressure on an exceeding a limit value of the actual ground pressure.

14. The work machine in accordance with claim 13, wherein a sensor apparatus is provided for an automatic measurement of the maximum permitted ground pressure.

15. The work machine in accordance with claim 13, wherein the work machine is a pile driver and/or a drill.

* * * * *